US011176460B2

(12) United States Patent
Zhao et al.

(10) Patent No.: US 11,176,460 B2
(45) Date of Patent: Nov. 16, 2021

(54) VISUAL ANALYSIS FRAMEWORK FOR UNDERSTANDING MISSING LINKS IN BIPARTITE NETWORKS

(71) Applicant: FUJI XEROX CO., LTD., Tokyo (JP)

(72) Inventors: Jian Zhao, Cupertino, CA (US);
Francine Chen, Menlo Park, CA (US);
Patrick Chiu, Mountain View, CA (US)

(73) Assignee: FUJIFILM Business Innovation Corp., Tokyo (JP)

( * ) Notice: Subject to any disclaimer, the term of this patent is extended or adjusted under 35 U.S.C. 154(b) by 425 days.

(21) Appl. No.: 16/194,877

(22) Filed: Nov. 19, 2018

(65) Prior Publication Data

US 2020/0160188 A1    May 21, 2020

(51) Int. Cl.
*G06N 5/02*       (2006.01)
*G06N 20/00*      (2019.01)

(52) U.S. Cl.
CPC ............ *G06N 5/022* (2013.01); *G06N 20/00* (2019.01)

(58) Field of Classification Search
CPC .......... G06N 5/02; G06N 5/022; G06N 20/00; G06N 20/20
See application file for complete search history.

(56) References Cited

U.S. PATENT DOCUMENTS

2018/0089318 A1* 3/2018 Chatterjee ........... G06F 16/9535
2019/0333256 A1* 10/2019 Xu ..................... G06F 16/9024

OTHER PUBLICATIONS

Xia et al., "Link Prediction for Bipartite Social Networks: The Role of Structural Holes", 2012, International Conference on Advances in Social Networks Analysis and Mining, 2012, pp. 153-157 (Year: 2012).*
Chang et al., "Exploring biological interaction networks with tailored weighted quasi-bicliques", 2012, BMC Bioinformatics, 13:S16, pp. 1-9 (Year: 2012).*
Stasko et al., "Jigsaw: Supporting Investigative Analysis through Interactive Visualization", IEEE Symposium on Visual Analytics Science and Technology, 2007, pp. 131-138 (Year: 2007).*
Grothaus et al., "Automatic layout and visualization of biclusters", 2006, Algorithms for Molecular Biology, vol. 15 (2006), pp. 1-11 (Year: 2006).*
Heinrich et al., "BiCluster Viewer: A Visualization Tool for Analyzing Gene Expression Data", 2011, Proceedings of the Conference on Advances in Visual Computing, vol. 2011, pp. 1-12 (Year: 2011).*

(Continued)

*Primary Examiner* — Ann J Lo
*Assistant Examiner* — Leonard A Sieger
(74) *Attorney, Agent, or Firm* — Procopio, Cory, Hargreaves & Savitch, LLP

(57) ABSTRACT

Example implementations described herein involve an interface for calculating and displaying missing links for data represented as a bipartite network, along with novel methods for improving link prediction algorithms in the related art. Through example implementations described herein, the accuracy of link prediction algorithms can be improved upon, thereby providing the user with a more accurate understanding of the data in the bipartite network.

16 Claims, 7 Drawing Sheets

(56) References Cited

OTHER PUBLICATIONS

Xu et al., "Interactive Visual Co-Cluster Analysis of Bipartite Graphs", 2016, IEEE Pacific Visualization Symposium, vol. 2016, pp. 32-39 (Year: 2016).*
Kapushesky et al., "Expression Profiler: next generation—an online platform for analysis of microarray data", 2004, Nucleic Acids Research, vol. 32, pp. 465-470 (Year: 2004).*
Theron et al., "BicOverlapper 2.0: Visual Analysis for Gene Expression", 2014, Bioinformatics, vol. 2014, pp. 1-2 (Year: 2014).*
Pech et al., "Link Prediction via Matrix Completion", 2016, arXiv, v1606.06812v2, pp. 1-7 (Year: 2016).*
Carrubba, C., et al., Legislative Voting Behaviour, Seen and Unseen: A Theory of Roll-Call Vote Selection, Legislative Studies Quarterly, 33(4), Nov. 2008, pp. 543-572.
Chang, Y-J., et al., Link Prediction in a Bipartite Network Using Wikipedia Revision Information, In 2012 Conference on Technologies and Applications of Artificial Intelligence, IEEE, Nov. 15-16, 2012, Tainan, Taiwan.
Fiaux, P., et al., Bixpolar: Visual Analytics with Biclusters, Computer, Aug. 2013, pp. 90-94.
Ghoniem, M., et al., On the Readability of Graphs Using Node-Link and Matrix-Based Representations: A Controlled Experiment and Statistical Analysis, Information Visualization, 4, 2005, pp. 114-135.
Grothaus, G. A., et al., Automatic Layout and Visualization of Biclusters, Algorithms for Molecular Biology, 2006, 1(15), 11 pgs.
Heckerman, D., et al., Probabilistic Entity-Relationship Models, PRMs and Plate Models, Proceedings of the 21st International Conference on Machine Learning, 2004, Banff, Canada, 6 pgs.
Heinrich, J., et al., Bicluster Viewer: A Visualization Tool for Analyzing Gene Expression Data, Advances in Visual Computing, Jul. 2011, pp. 641-652.
Henry, N., et al., NodeTrix: A Hybrid Visualization of Social Networks, IEEE Transactions on Visualization and Computer Graphics, 13(6), 2007, pp. 1302-1309.
Huang, Z., et al., Link Prediction Approach to Collaborative Filtering, JCDL '05 Proceedings of the 5th ACM/IEEE Joint Conference on Digital Libraries, Jun. 7-11, 2005, Denver, Colorado, pp. 141-142.
Isenberg, P., et al., Visualization Publications Dataset, IEEE Transactions on Visualization and Computer Graphics, 23(9), Sep. 2017, pp. 2199-2206, [online] [retrieved 2018] URL: https://sites.google.com/site/vispubdata/home.
Kapushesky, M., et al., Expression Profiler: Next Generation—An Online Platform for Analysis of Microarray Data, Nucleic Acids Research, 32, 2004, pp. W465-W470.
Keller, R., et al., Matrices or Node-Link Diagrams: Which Visual Representation is Better for Visualising Connectivity Models?, Information Visualization 2006, 5, pp. 62-76.
Liben-Nowell, D., et al., The Link-Prediction Problem for Social Networks, Journal of the American Society for Information Science and Technology, 58(7), 2007, pp. 1019-1031.
Lichtenwalter, R. Y., et al., Vertex Collocation Profiles: Subgraph Counting for Link Analysis and Prediction, In Proceedings of the 21st international Conference on Word Wide Web, WWW '12, Lyon, France, pp. 1019-1028.
Madeira, S. C., et al., Biclustering Algorithms for Biological Data Analysis: A Survey, IEEE Transactions on Computational Biology and Bioinformatics, 1(1), Jan.-Mar. 2004, pp. 24-45.
Martinez, V., et al., A Survey of Link Prediction in Complex Networks, ACM Computing Surveys, Dec. 2016 49(4), 34 pgs.
Santamaria, R., et al., BicOverlapper 2.0: Visual Analysis for Gene Expression, Bioinformatics, 2014, 30(12), pp. 1785-1786.
Scellato, S et al., Exploiting Place Features in Link Prediction on Location-Based Social Networks, In Proceedings of the 17th ACM SIGKDD International Conference on Knowledge Discovery and Data Mining, KDD '11, San Diego, California, Aug. 21-24, 2011, pp. 1046-1054.
Stasko, J., et al., Jigsaw: Supporting Investigative Analysis Through Interactive Visualization, Information Visualization, 2008, 7, pp. 118-132.
Streit, M., et al., Furby: Fuzzy Force-Directed Bicluster Visualization, BMC Bioinformatics, 2014, 15 (Suppl 6): S4, 13 pgs.
Sun, M., et al., BiSet: Semantic Edge Bundling with Biclusters for Sensemaking, IEEE Transactions on Visualization and Computer Graphics, 22(1), Jan. 2016, pp. 310-319.
Tong, H., et al., Fast Random Walk with Restart and Its Applications, In Proceedings of International Conference on Data Mining, IEEE, Dec. 2006, 12 pgs.
Wang, P., et al., Link Prediction in Social Networks: the State-of-the-Art, Science China Information Sciences, Jan. 2015, 58(1), 38 pgs.
Yu, K., et al., Gaussian Process Models for Link Analysis and Transfer Learning, Advances in Neural Information Processing Systems, 2008, pp. 1657-1664.
Zhang, Y., et al., On Finding Bicliques in Bipartite Graphs: A Novel Algorithm and its Application to the Integration of Diverse Biological Data Types, BMC Bioinformatics, 2014, 15(1): 110, 18 pgs.
Wohlfarth, T., et al., Semantic and Event-Based Approach for Link Prediction, Practical Aspects of Knowledge of Management, Springer Berlin-Heidelberg, 2008, pp. 50-61.
Xia, S., et al., Link Prediction for Bipartite Social Networks: The Role of Structural Holes, 2012 IEEE/ACM International Conference on Advances in Social Networks Analysis and Mining, Aug. 2012, pp. 153-157.

* cited by examiner

|  | | Atlantic Storm | Slack communication | VIS publications | Atlantic Storm* | Slack communication* |
|---|---|---|---|---|---|---|
| R-Precision | JA | .395 .428 .032 | .421 .424 .004 | .105 .126 .020 | .405 .423 .018 | .332 .341 .009 |
| | CN | .359 .580 .221 | .179 .424 .245 | .066 .129 .063 | .342 .552 .209 | .282 .339 .138 |
| | AA | .440 .455 .016 | .202 .219 .016 | .107 .152 .045 | .405 .418 .013 | .203 .218 .015 |
| | PA | .021 .585 .564 | .025 .590 .565 | .000 .012 .012 | .007 .226 .219 | .086 .422 .336 |
| | RW | .467 .531 .064 | .451 .464 .013 | .086 .112 .016 | .467 .552 .065 | .398 .407 .009 |
| AUC PR | JA | .388 .451 .053 | .301 .325 .024 | .039 .053 .014 | .393 .444 .051 | .225 .249 .024 |
| | CN | .305 .607 .302 | .148 .326 .178 | .025 .063 .039 | .300 .578 .277 | .133 .285 .152 |
| | AA | .388 .429 .031 | .170 .200 .030 | .039 .068 .029 | .379 .406 .027 | .152 .177 .025 |
| | PA | .008 .566 .557 | .021 .528 .507 | .000 .003 .002 | .005 .212 .207 | .055 .406 .352 |
| | RW | .435 .516 .082 | .346 .377 .031 | .039 .052 .013 | .448 .525 .078 | .279 .308 .029 |

JA: Jaccard coefficient; CN: common neighbors; AA: adamic-andar coefficient; PA: preferential attachment; RW: random walk.

FIG. 5

VISUAL ANALYSIS FRAMEWORK FOR UNDERSTANDING MISSING LINKS IN BIPARTITE NETWORKS

BACKGROUND

Field

The present disclosure relates generally to data analytics, and more specifically, for determining and visualizing missing links within bipartite networks.

Related Art

Many real-world complex systems can be modeled as bipartite networks (two-mode networks), where there are two types of nodes in a network and links only exist between different node types. Analyses of bipartite relationships have been used for data analytics in various application domains, such as studying political leanings with voter-vote networks based on roll call vote records, and investigating gene-expression networks in bioinformatics.

One analysis problem for such networks is link prediction (e.g., detecting missing links), which infers the existence of new relationships between nodes based on currently observed links. Such link production is valuable because real-world data may be noisy or incomplete. But normally the output of link prediction algorithms just contains a list of scores or probabilities for all predicted missing links, which is difficult to interpret, and these results can be inaccurate.

SUMMARY

In practice, analysts need to apply their domain knowledge to examine the algorithm output. To address the issues of the related art, a generic visual analysis framework for detecting and examining missing links in bipartite networks is proposed in the present disclosure. First, the framework contributes a novel link prediction approach for bipartite networks, which is an ensemble method leveraging the information of bicliques in the networks. Second, an interactive visualization is utilized to present detected missing links and allow for a better understanding of the meaning and influence of missing links, through two of the most common network analysis approaches: metric-based (e.g., computing node betweenness) and motif-based (e.g., detecting cliques).

Further, no related art system addressed the problems of detecting and visualizing missing links. More particularly, in example implementations, a matrix-based design is employed because links are the focus in our framework and need to be emphasized visually.

Further, common link prediction algorithms for networks roughly fall into two big categories: learning-based and similarity-based. The learning-based methods treat link prediction as a binary classification problem and train a machine learning model to predict the class label (i.e., positive for potential linking) for each non-connected node pairs. One related art approach is feature-based classification, which extracts features based on node attributes, topological structures, social theories, or combinations of them. Another is based on probabilistic graph models including relational model, entity-relationship model, and so forth. These techniques, although effective, are less general, which often require some extra information (e.g., semantic node attributes) in addition to the observed network structure. However, the trained machine learning models may only perform well on networks with certain characteristics (depending on the training set).

On the other hand, similarity-based methods attempt to compute a similarity score based on every non-connected pair of nodes and rank all these potential links. Ways of computing the similarity metrics include random-walk based simulation, and neighbor-based measures such as common neighbors, jaccard coefficient, adamic-adar coefficient, and preferential attachment. Researchers extended some of the similarity metrics to the bipartite network scenario. Example implementations move one step further by proposing a family of ensemble methods via integrating an important type of structural information in bipartite networks, bicliques, to improve the performance of the prediction.

Aspects of the present disclosure include a method, which can include for data represented as a bipartite network and for a set of missing links in the bipartite network, calculating a weight for each of the missing links in the set based on bicliques of the bipartite network; executing a link prediction algorithm configured to incorporate the weight for each of the missing links; and providing ones from the set of missing links selected by the link prediction algorithm as predicted missing links of the bipartite network.

Aspects of the present disclosure can further include a non-transitory computer readable medium, storing instructions for executing a process, the instructions involving, for data represented as a bipartite network and for a set of missing links in the bipartite network, calculating a weight for each of the missing links in the set based on bicliques of the bipartite network; executing a link prediction algorithm configured to incorporate the weight for each of the missing links; and providing ones from the set of missing links selected by the link prediction algorithm as predicted missing links of the bipartite network.

Aspects of the present disclosure include a system, which can include for data represented as a bipartite network and for a set of missing links in the bipartite network, means for calculating a weight for each of the missing links in the set based on bicliques of the bipartite network; means for executing a link prediction algorithm configured to incorporate the weight for each of the missing links; and means for providing ones from the set of missing links selected by the link prediction algorithm as predicted missing links of the bipartite network.

Aspects of the present disclosure include an apparatus, which can involve a processor, configured to, for data represented as a bipartite network and for a set of missing links in the bipartite network calculate a weight for each of the missing links in the set based on bicliques of the bipartite network; execute a link prediction algorithm configured to incorporate the weight for each of the missing links; and provide ones from the set of missing links selected by the link prediction algorithm as predicted missing links of the bipartite network.

BRIEF DESCRIPTION OF DRAWINGS

FIG. 5 illustrates the average performance of each condition of the experimental results in numbers.

DETAILED DESCRIPTION

Figure 1:
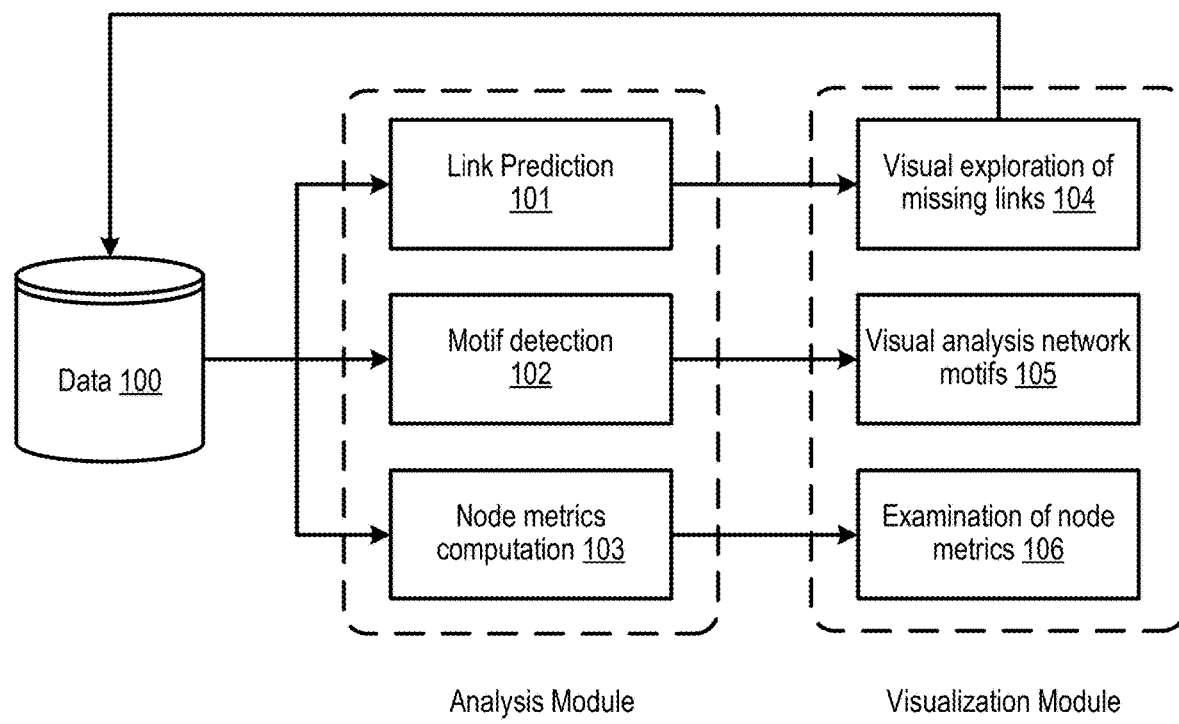
FIG. 1 illustrates an example system diagram, in accordance with an example implementation.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or administrator control over certain aspects of the implementation, depending on the desired implementation of one of ordinary skill in the art practicing implementations of the present application. Selection can be conducted by a user through a user interface or other input means, or can be implemented through a desired algorithm. Example implementations as described herein can be utilized either singularly or in combination and the functionality of the example implementations can be implemented through any means according to the desired implementations.

As set forth herein, the term "non-connected pair of nodes" is defined as the nodes that are not connected in the original network. The term "set of missing links" is defined as the potential links that exist between non-connected nodes. The term "predicted missing link" is defined as the missing links with the probability generated by the algorithm of example implementations described herein.

FIG. 1 illustrates an example system diagram, in accordance with an example implementation. In example implementations described herein, data 100 is processed through a framework that involves an analysis module and a visualization module. The analysis module supports missing link prediction in bipartite networks 101 as well as two of the most common ways for observing networks, including node metrics 103 and sub-network motifs 102. The link prediction method as described herein leverages the structural information of bicliques in the networks, which can be integrated with any related art similarity-based link prediction algorithms. The visualization module displays all the outputs from the analysis module and enables analysts to explore the data with rich user interactions. An analyst can visually investigate the identified missing links 104, network motifs 105, and node metrics 106, and further examine the influence of particular links by comparing the analytical results on the original network and the one with these links added.

Formally, a bipartite network can be defined as $G=\langle X, Y, E \rangle$, where X and Y are two nonoverlapping sets of nodes and E is the set of links that only exist between X and Y, i.e., $e=\langle x, y \rangle \in E$ where $x \in X$ and $y \in Y$. For a bipartite network, the number of all possible links is $|X| \cdot |Y|$ and we denote these links as U. Thus, a link prediction problem is to identify which links are likely missing in the set U–E.

Link prediction algorithms, specifically similarity-based methods, are used that first compute the similarity of every non-connected pair of nodes. Based on the similarity values, it can generate a ranked list of missing links with decreasing scores for recommendation. One way to compute the similarity between pairs of nodes is via a random walk. Another way of measuring similarity is based on comparing the neighborhoods of two nodes, including common neighbors, jaccard coefficient, adamic-adar coefficient, and preferential attachment.

Based on the above algorithms, example implementations described herein provide a novel approach that integrates one important type of structure in bipartite networks, bicliques (a.k.a., complete bipartite graphs). Formally, a biclique is defined as a sub-network, $G'=\langle X',Y',E' \rangle$, where $X' \subseteq X$, $Y' \subseteq Y$, and $E' \subseteq E$, and there exists a link $e=\langle x,y \rangle \in E'$ between every pair of nodes, $x \in X'$ and $y \in Y'$. Many algorithms have been proposed to efficiently detect all bicliques in a network, and in example implementations described herein, the Maximal Biclique Enumeration Algorithm (MBEA) algorithm is tested.

Figure 2:
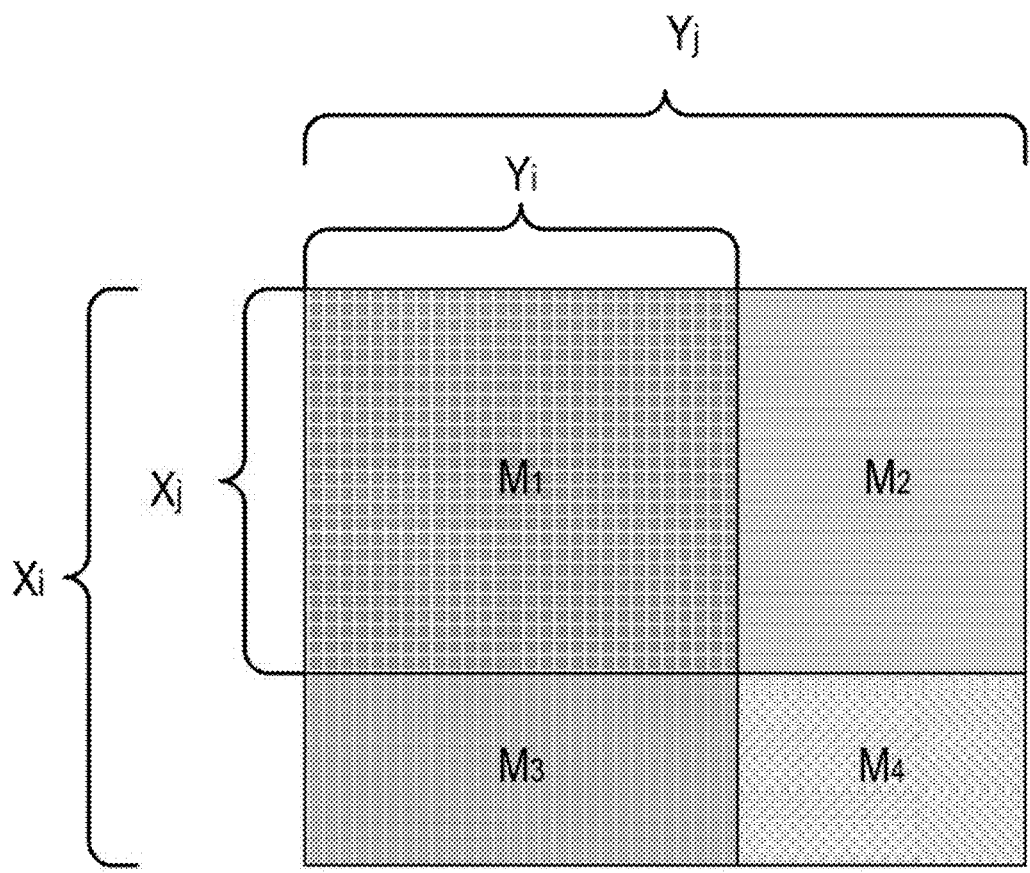
FIG. 2 illustrates bicliques in accordance with an example implementation.

FIG. 2 illustrates bicliques in accordance with an example implementation. Consider two bicliques as two communities that have some nodes in common; each missing link between the non-overlapping nodes from the two communities contributes to the formation of a bigger community that benefits all the nodes. If the two communities have many nodes in common, each of the few missing links that can be added carries more value, as a bigger biclique can be formed fairly easily. On the other hand, if the two communities have less in common, then many more links need to be added to merge the two bicliques into a larger one, and each of the missing links carries less value.

Following this intuition, example implementations involve an algorithm to re-rank the missing link lists generated by the above similarity-based methods. In example implementations, the proposed algorithm computes weights, $w_e$, for all missing links (in $M_4$ in FIG. 2) based on the information of bicliques in the network. The weight of a link is the sum of all the values calculated when processing each pair of bicliques, in which the value is determined by the sizes of the difference of the two bicliques and their overlap. Intuitively, as shown in FIG. 2, the value computed in each iteration corresponds to the area of the intersection $M_1$ divided by the area of the missing part $M_4$. Then, the weights and the similarity scores are normalized by their maximum values, and generate a new ranked list with the new scores with $s'(x,y)=w(x,y) \cdot x(x,y)$. The above approach can be used together with any existing common similarity-based link prediction to produce a family of algorithms.

However, algorithms are not perfect; the missing link prediction can be wrong. That is because real-world scenarios are far more complicated, and it is difficult to consider every nuance in all domains for the algorithm design. An analyst's prior knowledge is needed for further examination of the outputs from the algorithm, which combines the flexibility of humans and the scalability of machines.

Figure 3:
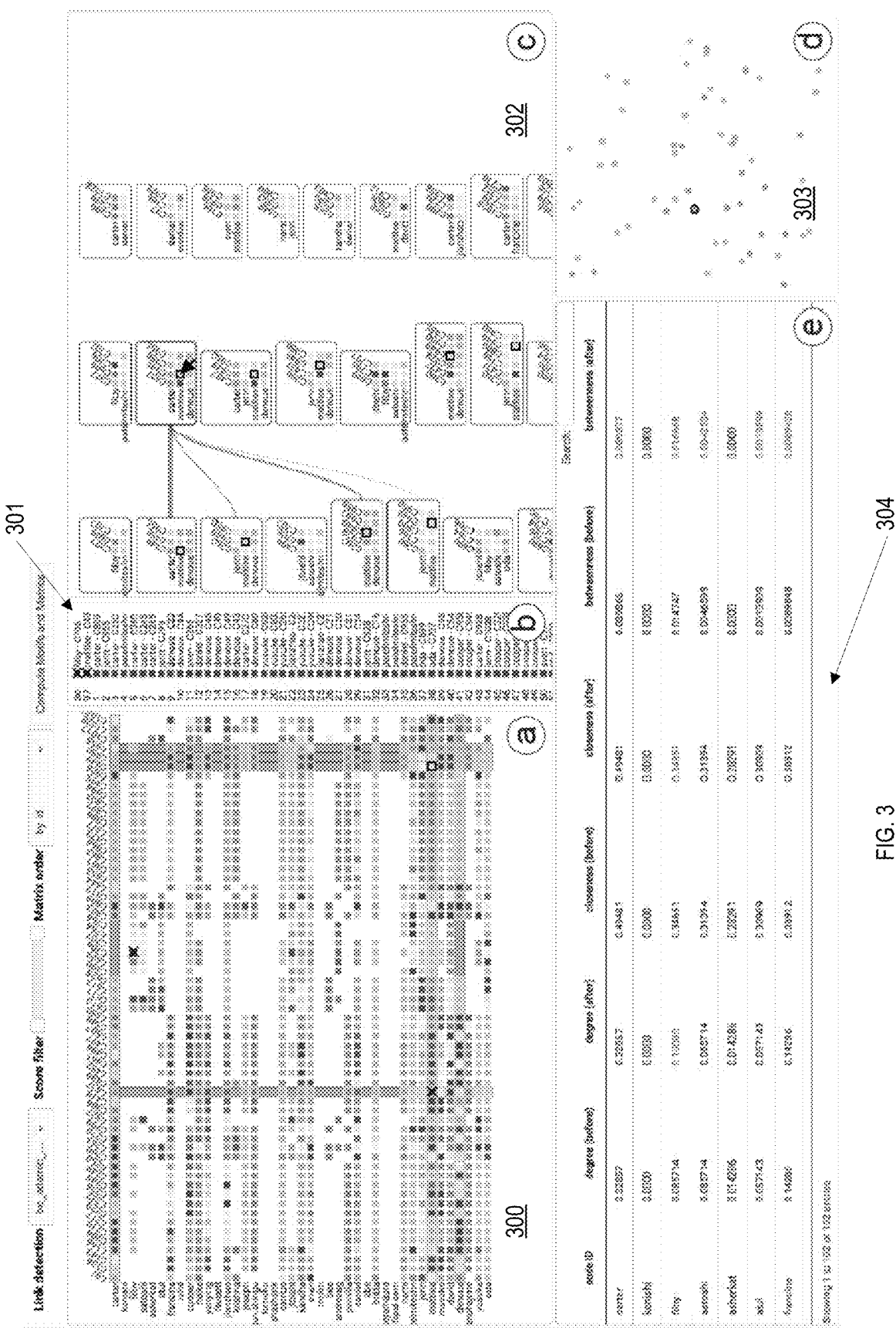
FIG. 3 illustrates an example interface for facilitating the visual exploration of missing links, in accordance with an example implementation.

Example implementations involve a visual interface to help analysts better make sense of the missing links identified by the aforementioned methods in bipartite networks. This visualization module involves five interactively-coordinated views: a Network View and a Link List View to support the exploration of missing links, a Motifs Overview and a Detail View to offer the analysis of motifs, and a Metrics View to display node-based metrics as illustrated in FIG. 3. These views present the outputs from the analysis module in visual forms to allow analysts to effectively answer the what, why, and how questions about missing links.

FIG. 3 illustrates an example interface for facilitating the visual exploration of missing links, in accordance with an example implementation. In the example interface of FIG. 3, there are several views. First, the Network View 300 as shown in interface pane (a), displays the bi-adjacency matrix of a bipartite network, where the row and the column represent two different types of nodes respectively. The links can be represented as squares in the intersections of rows and columns. The existing links in the network can be shown in a first color scale (e.g., yellow-green), where the hue reflects the weight of a link. If it is an unweighted network, all the links are shown in the darkest hue (e.g., green). The predicted missing links are displayed in a second color scale (e.g., white-purple), where a darker color reflects higher probability or score determined by the link prediction algorithm.

Further, the Link List View 301 as shown in interface pane (b) is configured to present the missing links linearly by probability or score, where each link is visualized in a similar fashion with that in the Network View 300. Additional information such as the rank and the connecting nodes of the link is provided. This Link List View 301 works together with the Network View 300, allowing an analyst to better make sense of the missing link prediction in different perspectives.

In example implementations, various interface functions are provided. In the Network View 300, an analyst can reorder the rows and columns of the matrix with certain criteria such as the node label, the average prediction score, and the total number of detected missing links. An analyst can also filter the matrix based on the prediction score, for example, to reveal the most probable missing links suggested by the algorithm. Moreover, different link prediction algorithms can be applied and viewed in the visualization to allow for an easy comparison of the results.

Further, an analyst can explore the link prediction results and add certain missing links to examine their influence with visual analysis of motifs and metrics described in the following. The added links are marked (e.g., as black crosses) on the matrix and also displayed at the top of the list. Individual links or a group of links can be added at once by selecting them from the matrix.

Motif analysis is one main approach to understanding the topology of a network. In bipartite networks, a biclique is one of the most important structural patterns. In the interface pane (c), there is a Detail View 302, and an overview 303 provided in interface pane (d) for browsing the motifs at different scales. These two views offer the visual exploration of all bicliques detected in the network, and the investigation of the changes of results if certain missing links are added. In the Motifs Detail View 302, bicliques are shown as small multiples of matrices in similar visual encodings with the Network View 300. Essentially, a biclique is a portion of the bi-adjacency matrix of the entire network. In addition, the Motifs Overview 303 displays all the bicliques as dots in a two-dimensional space based on the Multidimensional scaling (MDS) projection. The distance between two bicliques is measured with the sum of the Jaccard distance between their node sets of each type.

To support the comparison of two sets of bicliques detected in the networks with and without added links by an analyst, the Motifs Detail View 302 organizes the bicliques in three columns: removed bicliques, newly-added ones, and unchanged ones, compared to the biclique set of the original network; they are in borders represented by different colors (e.g., red, green, and gray). In each column, the default order of bicliques is by size, which can be changed to other sorting criteria. Similarly, the Motifs Overview 303 encodes these bicliques in the three different colors.

Further, the similarity between the added and removed bicliques can be computed using the Jaccard distance to facilitate a better understanding of the structural changes and the influence of missing links. In the Motifs Detail View 302, when an analyst hovers over a biclique, this information is shown as links connecting the related bicliques, with the thickness of the links mapped to their pairwise similarity value.

Computing node-metrics is a method used for getting a picture of the characteristics of a network in social sciences and other domains. The Metrics View 304 in interface pane (e) supports this kind of analysis by presenting a number of metrics in a traditional tabular view, including the degree, closeness, and betweenness centralities of before and after adding certain missing links. Changes of metric values are highlighted (e.g., in red). This table is also interactively linked with other views. For example, hovering over a row emphasizes the corresponding node in the Network View 301. As there might a large number of nodes (rows), a search function can also be provided, and hovering over a node in other views automatically navigates to the corresponding row in the table.

To validate the accuracy of the proposed missing link prediction approach, quantitative experiments were conducted with three bipartite networks, including a weighted person-place network extracted from the Atlantic Storm corpus, a weighted user-conversation bipartite network detected from Slack communication messages, and an unweighted bipartite network between authors and papers from the IEEE VIS publication corpus.

As there is no ground truth for missing links, the test randomly removed a certain number of links from an original network, applied the link prediction algorithms on this new network, and measured the performance by comparing the detected missing links with the removed (actually missing) links, i.e., the ground truth. To validate the ensemble approach, five existing link prediction algorithms were integrated into the approach, including common neighbors, jaccard coefficient, adamic-adar coefficient, preferential attachment, and random walk methods. For each algorithm, to test its performance under different situations, the test randomly removed 1%, 2%, 5%, 10%, and 15% of links from an input network. For each of these conditions, the experiment was performed with random link removal five times, in order to reduce sampling bias.

Figure 4A:
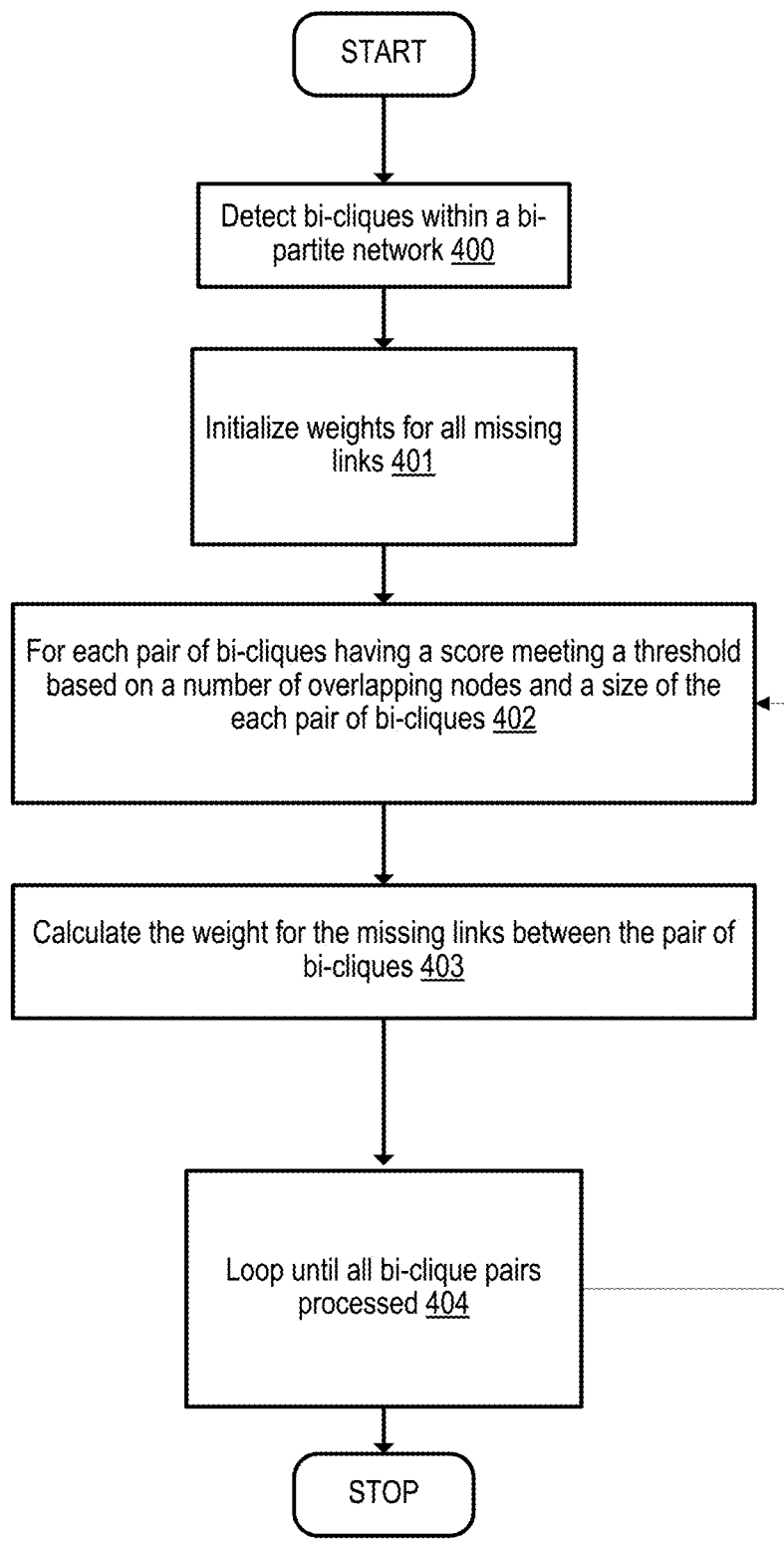
FIGS. 4(*a*) and 4(*b*) illustrate example flow diagrams, in accordance with an example implementation.

FIG. 4(a) illustrates an example flow for the proposed algorithm, in accordance with an example implementation.

At 400, the flow detects bicliques within a bipartite network $G=\langle X, Y, E \rangle$ and incorporates them into a list $L=\{C_i=\langle X_i, Y_i, E_i \rangle\}$, with X and Y each being the set of nodes within the respective network of the bipartite network, and E representing the links that exist in the bipartite network. Bicliques can be detected by any method according to the desired implementation.

At 401, the flow initializes weights for all missing links $e \in U-E$, $U=\{\forall \langle x, y \rangle; x \in X, y \in Y\}$, wherein U is the set of all possible links that could exist in the bipartite network. In an example implementation, the flow sets $w_e \leftarrow 0$ or other base value in accordance with the desired implementation.

At 402, for each pair of bicliques $(C_i, C_j)$ from list L having a score o meeting a threshold based on a number of overlapping nodes and a size of the each pair of bicliques, the flow conducts calculations for the weight of the missing links as described in 403. In an example implementation, the score can be based on a number of overlapping nodes meeting a threshold and a size of the each pair of bicliques, and a threshold can accordingly be set to the desired implementation. An example formula for calculating the score o can be as follows:

$$o \leftarrow \frac{|X_i \cap X_j| \cdot |Y_i \cap Y_j|}{|X_i \cup X_j| \cdot |Y_i \cup Y_j|}$$

If o fails to meet a threshold, then the biclique pair is discarded and the next biclique pair is then considered. Otherwise, the flow proceeds to 403 to calculate the weight for the missing links between the pair of bicliques. An example calculation can be in an incremental manner based on the number of overlapping nodes between the biclique pair and the impact that a link would have based on the corresponding values of the nodes (e.g., size of the biclique pair). In an example implementation, a formula for doing such calculations can include:

$$w_e \leftarrow w_e + \frac{|X_i \cap X_j| \cdot |Y_i \cap Y_j|}{|X_i - X_j| \cdot |Y_j - Y_i| + |X_j - X_i| \cdot |Y_i - Y_j|}$$

At 404, the flow proceeds to loop back to the flow of 403 until all biclique pairs are processed.

Figure 4B:
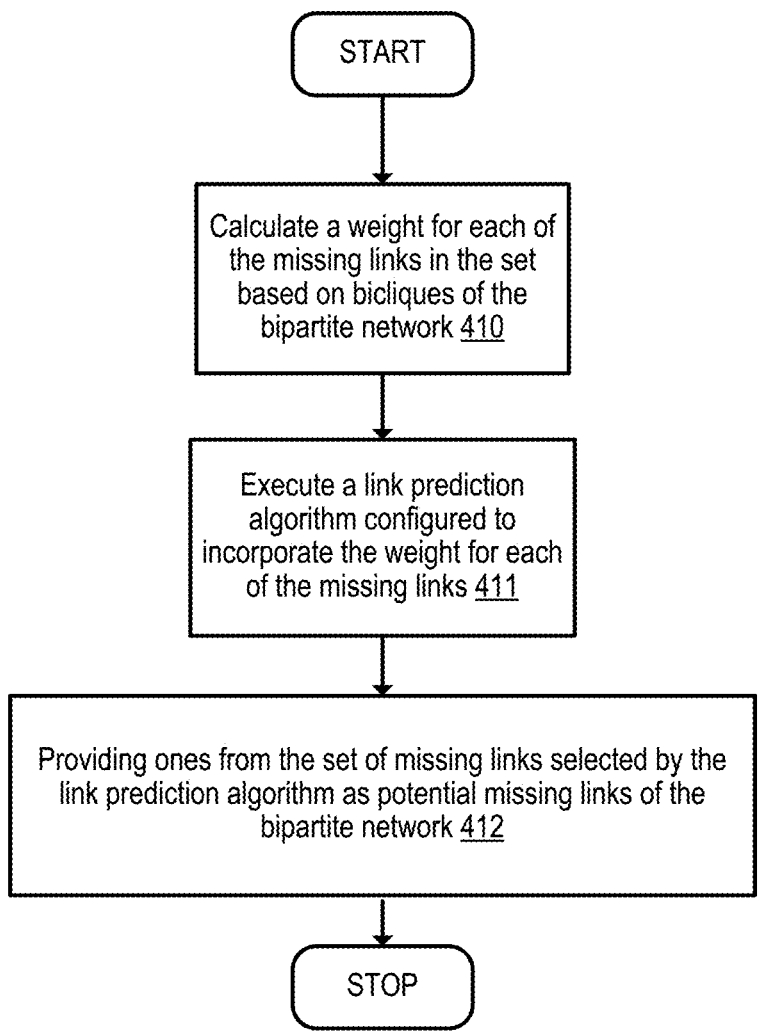

FIG. 4(b) illustrates an example overall flow, in accordance with an example implementation. Given data represented as a bipartite network and a set of missing links in the bipartite network, at 410 the algorithm of FIG. 4(a) is executed for calculating a weight for each of the missing links in the set based on bicliques of the bipartite network.

At 411 the flow executes a link prediction algorithm configured to incorporate the weight for each of the missing links. Any link prediction algorithm known in the art can be utilized for this purpose such as the algorithms described herein.

At 412, the flow provides ones from the set of missing links selected by the link prediction algorithm as predicted missing links of the bipartite network as illustrated in FIG. 3. This can involve presenting the bipartite network as a bi-adjacency matrix involving rows that represent a first type of node in the bipartite network, and columns that represent rows of a second type of node in the bipartite network, each of the entries in the matrix representing a link between the first type of node and the second type of node, as illustrated in FIG. 3. The link prediction algorithm can select the predicted missing links based on the score obtained by the link prediction algorithm for a particular link meeting a threshold, or all of the missing links can be displayed in the bi-adjacency matrix depending on the desired implementation. As illustrated in FIG. 3, the providing ones from the set of missing links selected by the link prediction algorithm as the predicted missing links of the bipartite network can involve representing the entry as a color hue according to a score provided by the link prediction algorithm. Further as described in FIG. 3, the presenting the bipartite network can involve providing an interface configured to order the rows and columns of the bi-adjacency matrix according to a selected criteria (type of node, average score, etc.). Further as illustrated in FIG. 3, providing the ones from the set of missing links selected by the link prediction algorithm as the predicted missing links of the bipartite network can involve presenting the predicted missing links linearly by probability.

FIG. 5 illustrates the average performance of each condition of the experimental results in numbers. For each condition (i.e., in a table cell), the three numbers indicate (1) the average metric of the baseline, (2) the average metric of the proposed method, and (3) the improvement of the proposed method over the five runs (on removing different numbers of links from the original dataset). The highest performance and improvement are highlighted in bold for each metric in each dataset. The performance metrics (R-Precision or Area Under Curve—Precision Recall (AUC PR)) are computed in each run with the input network built by removing a certain percentage of the links.

From the results, the proposed biclique oriented methods enhance their baselines in all the conditions with different levels of improvement on both R-Precision and AUC PR. Some of the performance gain is substantial, where the maximum improvement appears with the preferential attachment algorithm for the unweighted Atlantic Storm dataset (0.564 for R-Precision and 0.557 for AUC PR). Thus, through the implementations of the algorithms as described in FIGS. 4(a) and 4(b), improvement to related art algorithms can be achieved and related art link prediction algorithms can be enhanced to more accurately detect missing links.

Such example implementations are particularly applicable to big data analytics in which there is a large volume of data and the data includes real world data that may be noisy. For example, for data utilized in determining gene expression, genes are related to different conditions, and the bipartite network involves a first type of node (genes) and a second type of node (conditions/diseases that can occur). In practice, conducting experiments for every type of gene combination is impractical because the conditions and genes are too numerous. Through example implementations, analysis can be done on such a bipartite network to identify which combination of genes are likely to cause which conditions through missing link detection, and then the users can focus on those particular gene/condition experiments.

In another example implementation involving drug discovery, the bipartite network can involve different types of molecules and different types of conditions (e.g., side effects, disease treatment efficacy). Drug discovery can involve an inordinate amount of experimentation as there can be too many different types of molecules and conditions that the user may be interested in. By applying the algorithms as described herein, the causation between drug molecule combinations and conditions can be more accurately determined than link prediction algorithms of the related art, and thus the user can focus the drug experiments to test such conditions accordingly.

Figure 6:
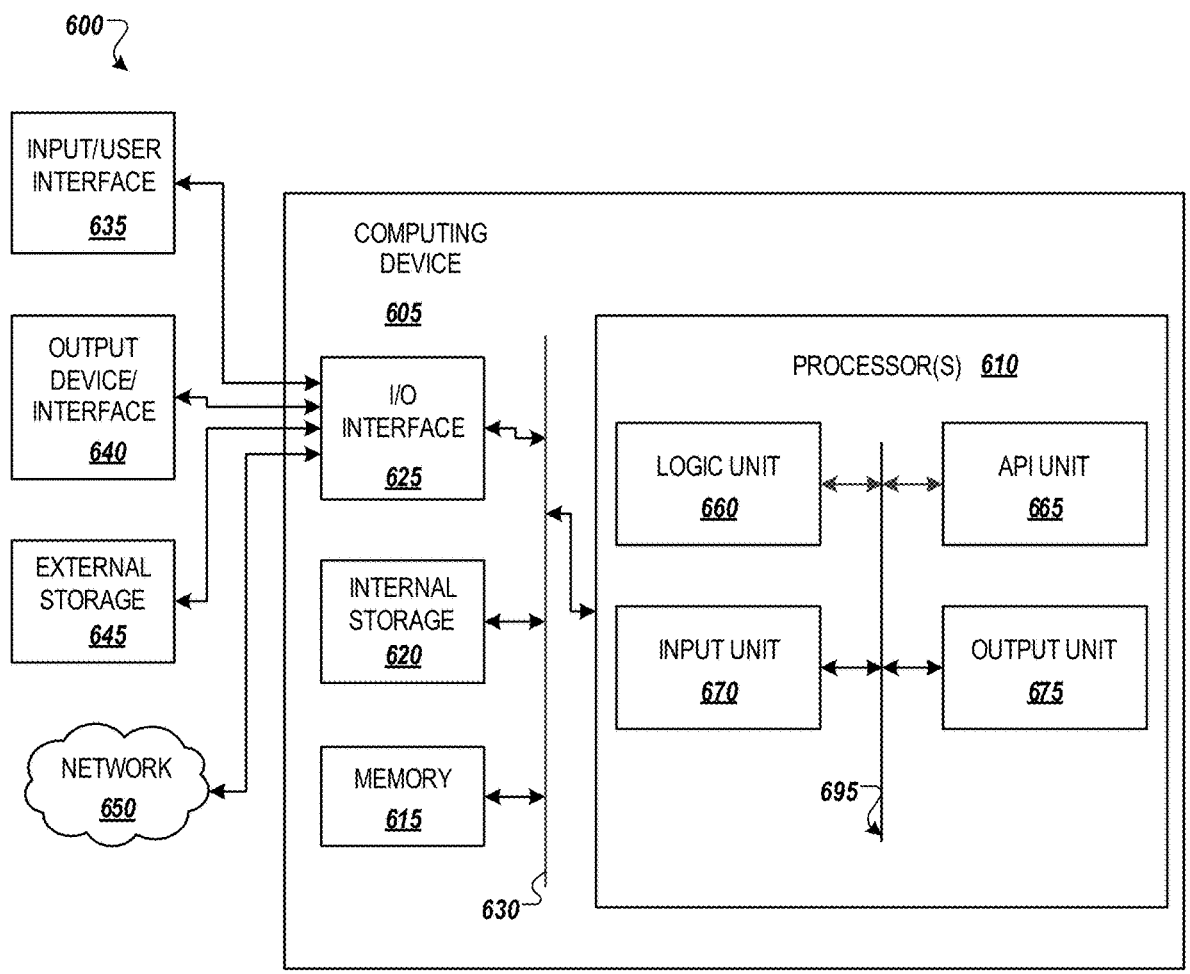
FIG. 6 illustrates an example computing environment with an example computer device suitable for use in example implementations.

FIG. 6 illustrates an example computing environment with an example computer device suitable for use in example implementations. Computer device 605 in computing environment 600 can include one or more processing units, cores, or processors 610, memory 615 (e.g., RAM, ROM, and/or the like), internal storage 620 (e.g., magnetic, optical, solid state storage, and/or organic), and/or I/O interface 625, any of which can be coupled on a communication mechanism or bus 630 for communicating information or embedded in the computer device 605.

Computer device 605 can be communicatively coupled to input/user interface 635 and output device/interface 640. Either one or both of input/user interface 635 and output device/interface 640 can be a wired or wireless interface and can be detachable. Input/user interface 635 may include any device, component, sensor, or interface, physical or virtual, that can be used to provide input (e.g., buttons, touch-screen interface, keyboard, a pointing/cursor control, microphone, camera, braille, motion sensor, optical reader, and/or the like). Output device/interface 640 may include a display, television, monitor, printer, speaker, braille, or the like. In some example implementations, input/user interface 635 and output device/interface 640 can be embedded with or physically coupled to the computer device 605. In other example implementations, other computer devices may function as or provide the functions of input/user interface 635 and output device/interface 640 for a computer device 605. In example implementations involving a touch screen display, a television display, or any other form of display, the display is configured to provide a user interface as illustrated, for example, at FIG. 3.

Examples of computer device 605 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, other computers, information kiosks, televisions with one or more processors embedded therein and/or coupled thereto, radios, and the like).

Computer device 605 can be communicatively coupled (e.g., via I/O interface 625) to external storage 645 and network 650 for communicating with any number of networked components, devices, and systems, including one or more computer devices of the same or different configuration. Computer device 605 or any connected computer device can be functioning as, providing services of, or referred to as a server, client, thin server, general machine, special-purpose machine, or another label.

I/O interface 625 can include, but is not limited to, wired and/or wireless interfaces using any communication or I/O protocols or standards (e.g., Ethernet, 802.11x, Universal System Bus, WiMax, modem, a cellular network protocol, and the like) for communicating information to and/or from at least all the connected components, devices, and network in computing environment 600. Network 650 can be any network or combination of networks (e.g., the Internet, local area network, wide area network, a telephonic network, a cellular network, satellite network, and the like).

Computer device 605 can use and/or communicate using computer-usable or computer-readable media, including transitory media and non-transitory media. Transitory media include transmission media (e.g., metal cables, fiber optics), signals, carrier waves, and the like. Non-transitory media include magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computer device 605 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C #, Java, Visual Basic, Python, Perl, JavaScript, and others).

Memory 615 may be configured to store or manage algorithms to be executed by processor(s) 610 as described in the flow, for example, at FIGS. 4(*a*) and 4(*b*) along with the data to be processed. The example implementations as described herein may be conducted singularly, or in any combination of each other according to the desired implementation and are not limited to a particular example implementation.

Processor(s) 610 can execute under any operating system (OS) (not shown), in a native or virtual environment. One or more applications can be deployed that include logic unit 660, application programming interface (API) unit 665, input unit 670, output unit 675, and inter-unit communication mechanism 695 for the different units to communicate with each other, with the OS, and with other applications (not shown). The described units and elements can be varied in design, function, configuration, or implementation and are not limited to the descriptions provided. Processor(s) 610 can be in the form of physical processors or central processing units (CPU) that is configured to execute instructions loaded from Memory 615.

In some example implementations, when information or an execution instruction is received by API unit 665, it may be communicated to one or more other units (e.g., logic unit 660, input unit 670, output unit 675). In some instances, logic unit 660 may be configured to control the information flow among the units and direct the services provided by API unit 665, input unit 670, output unit 675, in some example implementations described above. For example, the flow of one or more processes or implementations may be controlled by logic unit 660 alone or in conjunction with API unit 665. The input unit 670 may be configured to obtain input for the calculations described in the example implementations, and the output unit 675 may be configured to provide output based on the calculations described in example implementations.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of defined steps leading to a desired end state or result. In example implementations, the steps carried out require physical manipulations of tangible quantities for achieving a tangible result.

Unless specifically stated otherwise, as apparent from the discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer-readable storage medium or a computer-readable signal medium. A computer-readable storage medium may involve tangible mediums such as, but not limited to optical disks, magnetic disks, read-only memories, random access memories, solid state devices and drives, or any other types of tangible or non-transitory media suitable for storing electronic information. A computer readable signal medium may include mediums such as carrier waves. The algorithms and displays presented herein are not inherently related to any particular computer or other apparatus. Computer programs can involve pure software implementations that involve instructions that perform the operations of the desired implementation.

Various general-purpose systems may be used with programs and modules in accordance with the examples herein, or it may prove convenient to construct a more specialized apparatus to perform desired method steps. In addition, the example implementations are not described with reference to any particular programming language. It will be appreciated that a variety of programming languages may be used to implement the teachings of the example implementations as described herein. The instructions of the programming language(s) may be executed by one or more processing devices, e.g., central processing units (CPUs), processors, or controllers.

As is known in the art, the operations described above can be performed by hardware, software, or some combination of software and hardware. Various aspects of the example implementations may be implemented using circuits and logic devices (hardware), while other aspects may be implemented using instructions stored on a machine-readable medium (software), which if executed by a processor, would cause the processor to perform a method to carry out implementations of the present application. Further, some example implementations of the present application may be performed solely in hardware, whereas other example implementations may be performed solely in software. Moreover, the various functions described can be performed in a single unit, or can be spread across a number of components in any number of ways. When performed by software, the methods may be executed by a processor, such as a general purpose computer, based on instructions stored on a computer-readable medium. If desired, the instructions can be stored on the medium in a compressed and/or encrypted format.

Moreover, other implementations of the present application will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

What is claimed is:

1. A method, comprising:
   for data represented as a bipartite network and for a set of missing links in the bipartite network:
   calculating a weight for each of the missing links in the set based on bicliques of the bipartite network;
   executing a link prediction algorithm configured to incorporate the weight for each of the missing links; and
   providing ones from the set of missing links selected by the link prediction algorithm as predicted missing links of the bipartite network, wherein the providing by the link prediction algorithm comprises providing a score for each predicted missing link that indicates a probability that a respective predicted missing links exists between respective nodes, and
   presenting the bipartite network as a bi-adjacency matrix comprising rows that represent a first type of node in the bipartite network, and columns that represent rows of a second type of node in the bipartite network, each of the entries in the matrix representing one link between a node of the first type and a node of the second type,
   wherein the providing ones from the set of missing links selected by the link prediction algorithm as the predicted missing links of the bipartite network comprises providing, by the link prediction algorithm, a score for each of the predicted missing links that indicates a probability that a respective predicted missing link exists between a respective node of the first type and a respective node of the second type, and
   wherein the presenting the bipartite network comprises providing an interface configured to represent each of the entries in the matrix as a color hue according to the score, and configured to order the rows and columns of the bi-adjacency matrix according to a selected criteria.

2. The method of claim 1, wherein the calculating the weight for the each of the missing links in the set based on bicliques of the bipartite network comprises:
   for each pair of bicliques having a score based on a number of overlapping nodes meeting a threshold and a size of the each pair of bicliques, calculating the weight for ones of the set of missing links between the pair of bicliques.

3. The method of claim 2, wherein the calculating the weight for ones of the set of missing links between the each pair of bicliques is based on the number of overlapping nodes and the size of the each pair of bicliques.

4. The method of claim 1, wherein providing the ones from the set of missing links selected by the link prediction algorithm as the predicted missing links of the bipartite network comprises presenting the predicted missing links linearly by probability.

5. A non-transitory computer readable medium, storing instructions for executing a process, the instructions comprising:
   for data represented as a bipartite network and for a set of missing links in the bipartite network:
   calculating a weight for each of the missing links in the set based on bicliques of the bipartite network;
   executing a link prediction algorithm configured to incorporate the weight for each of the missing links; and
   providing ones from the set of missing links selected by the link prediction algorithm as predicted missing links of the bipartite network, wherein the providing by the link prediction algorithm comprises providing a score for each predicted missing link that indicates a probability that a respective predicted missing links exists between respective nodes, and
   presenting the bipartite network as a bi-adjacency matrix comprising rows that represent a first type of node in the bipartite network, and columns that represent rows of a second type of node in the bipartite network, each of the entries in the matrix representing one link between a node of the first type and a node of the second type,
   wherein the providing ones from the set of missing links selected by the link prediction algorithm as the predicted missing links of the bipartite network comprises providing, by the link prediction algorithm, a score for each of the predicted missing links that indicates a probability that a respective predicted missing link exists between a respective node of the first type and a respective node of the second type, and
   wherein the presenting the bipartite network comprises providing an interface configured to represent each of the entries in the matrix as a color hue according to the score, and configured to order the rows and columns of the bi-adjacency matrix according to a selected criteria.

6. The non-transitory computer readable medium of claim 5, wherein the calculating the weight for the each of the missing links in the set based on bicliques of the bipartite network comprises:

for each pair of bicliques having a score based on a number of overlapping nodes meeting a threshold and a size of the each pair of bicliques, calculating the weight for ones of the set of missing links between the pair of bicliques.

7. The non-transitory computer readable medium of claim 6, wherein the calculating the weight for ones of the set of missing links between the each pair of bicliques is based on the number of overlapping nodes and the size of the each pair of bicliques.

8. The non-transitory computer readable medium of claim 5, wherein providing the ones from the set of missing links selected by the link prediction algorithm as the predicted missing links of the bipartite network comprises presenting the predicted missing links linearly by probability.

9. An apparatus, comprising:
a processor configured to:
for data represented as a bipartite network and for a set of missing links in the bipartite network:
calculate a weight for each of the missing links in the set based on bicliques of the bipartite network;
execute a link prediction algorithm configured to incorporate the weight for each of the missing links; and
provide ones from the set of missing links selected by the link prediction algorithm as predicted missing links of the bipartite network, wherein the providing by the link prediction algorithm comprises providing a score for each predicted missing link that indicates a probability that a respective predicted missing links exists between respective nodes, and
present the bipartite network as a bi-adjacency matrix comprising rows that represent a first type of node in the bipartite network, and columns that represent rows of a second type of node in the bipartite network, each of the entries in the matrix representing one link between a node of the first type and a node of the second type,
wherein the providing ones from the set of missing links selected by the link prediction algorithm as the predicted missing links of the bipartite network comprises providing, by the link prediction algorithm, a score for each of the predicted missing links that indicates a probability that a respective predicted missing link exists between a respective node of the first type and a respective node of the second type, and
wherein the presenting the bipartite network comprises providing an interface configured to represent each of the entries in the matrix as a color hue according to the score, and configured to order the rows and columns of the bi-adjacency matrix according to a selected criteria.

10. The apparatus of claim 9, wherein the processor is configured to calculate the weight for the each of the missing links in the set based on bicliques of the bipartite network by:

for each pair of bicliques having a score based on a number of overlapping nodes meeting a threshold and a size of the each pair of bicliques, calculating the weight for ones of the set of missing links between the pair of bicliques.

11. The apparatus of claim 10, wherein the processor is configured to calculate the weight for ones of the set of missing links between the each pair of bicliques is based on the number of overlapping nodes and the size of the each pair of bicliques.

12. The apparatus of claim 9, wherein the processor is configured to provide the ones from the set of missing links selected by the link prediction algorithm as the predicted missing links of the bipartite network by presenting the predicted missing links linearly by probability.

13. The apparatus of claim 9, wherein the processor is configured to:
in response to a selection on an interface of one of the predicted missing links:
conducting at least one of motif analysis or metric analysis on the selected one of the predicted missing links through adding the one of the predicted missing links in the bipartite network; and
providing a result of the at least one of the motif analysis or the metric analysis for the selected one of the predicted missing links.

14. The method of claim 1, wherein each of the entries in the matrix for the missing links are represented according to a first color scale, wherein the interface is configured to represent existing links between a node of the first type and a node of the second type according a second color scale different than the first color scale.

15. The method of claim 1, wherein the interface is configured to reorder the rows and columns of the bi-adjacency matrix according to selected criteria, each selected criteria corresponding to a different order, wherein the selected criteria comprises one of a node label, an average prediction score, and a total number of missing links.

16. The method of claim 1, wherein the interface is configured to add a missing link as an entity in response to an input identifying an entity of the matrix.

* * * * *